United States Patent [19]

Yanovsky

[11] Patent Number: 4,609,630

[45] Date of Patent: Sep. 2, 1986

[54] METHOD FOR IMPROVING THE SPECIFICITY OF IMMUNOASSAYS

[76] Inventor: Jorge F. Yanovsky, 290 Ferrari St., 1414 Buenos Aires, Argentina

[21] Appl. No.: 583,262

[22] Filed: Feb. 24, 1984

[30] Foreign Application Priority Data

Mar. 23, 1983 [AR] Argentina ............................. 292484
Jan. 20, 1984 [AR] Argentina ............................. 295500

[51] Int. Cl.⁴ ................. G01N 33/554; G01N 33/555; G01N 33/556
[52] U.S. Cl. ..................... 436/519; 436/520; 436/521; 436/825; 436/827
[58] Field of Search .............. 436/825, 826, 827, 536, 436/517, 519, 520, 824, 521

[56] References Cited

U.S. PATENT DOCUMENTS

| | | | |
|---|---|---|---|
| 4,140,754 | 2/1979 | Iwasa | 436/520 |
| 4,292,038 | 9/1981 | Kondo et al. | 436/825 X |
| 4,298,346 | 11/1981 | Ito | 436/520 |
| 4,362,531 | 12/1982 | de Steenwinkel | 436/825 |
| 4,403,042 | 9/1983 | Henry et al. | 436/825 X |

OTHER PUBLICATIONS

Barondes, S. H. (1984), Science, 223: 1259–1264.
M. C. Stuart et al., Clinical Chemistry, 27(1), 52–56 (1981).
J. Mohr et al., Chemical Abstracts, 99: 172385q (1983).

*Primary Examiner*—Christine M. Nucker
*Assistant Examiner*—Jack Spiegel
*Attorney, Agent, or Firm*—Browdy and Neimark

[57] ABSTRACT

A method and serological reagent for determining antigens or antibodies with enhanced sensitivity and specificity techniques acts in an interdependent manner in one diagnostic unit of two separately acting components. This action can be simultaneous or consecutive and the combined effect inhibits "lectin-like" factors or "unspecific antibodies" and detects specific antibodies or antigens.

5 Claims, No Drawings

METHOD FOR IMPROVING THE SPECIFICITY OF IMMUNOASSAYS

BACKGROUND OF INVENTION

The diagnosis of a great number of contagious diseases is based on the evalution of the immunological response generated by the hosts against the invading infectious agents.

The methodologies for these types of studies are plentiful but nearly all of them are based on a similar principle; this principle consists in the quantification or semiquantification of the antibodies generated against the microorganisms causing the disease. This type of investigation falls within the specialty termed serology, and it is an indirect way of inferring the existence of a disease. In fact, it is argued that if a person possesses antibodies against a certain infectious agent, this is due to the fact that this agent or components of same (antigens) are causing an immunological stimulation of the host, and consequently the generation of antibodies could be assumed to mean that the infectious agent is present.

It is thus obvious that the efficiency of the system will depend on how reliably we can assign to each detection of antibodies its true correspondence with a certain antigen or microorganism. It is also obvious that the efficiency of the system will depend on the levels of detection of antibodies that can be achieved.

These two aspects are generally known as the specificity and sensitivity of serological tests. Of the two, sensitivity is perhaps easier to achieve as far as instruments are concerned, because due to the evolution and improvement of methods for measuring biological molecules, including radioisotopes, enzymes, etc., it is possible to detect infinitesimal quantities of any immunologically interesting protein.

Specificity is more difficult to deal with. Implicit in this question are problems derived from the antigenic stimulus and problems derived from the very responses whether natural or triggered by the stimulated host.

A great number of antigens are widely distributed in nature and repeated among living creatures. It is quite common, accordingly, that the response against one of them is capable of reacting simultaneously against several owners of the same.

In the course of the past 30 or 40 years, scientists doing research work in the field of immunochemistry have attached special importance to the search for antigens having a unique identity for the preparation of serological reagents. In some cases, these efforts have met with success. Nevertheless, they are not easy to accomplish and very often they are followed by a substantial reduction of the sensitivity inherent in the system.

It is obvious that the search for specific components of a microbial agent should be accompanied by a selection in which some components are dismissed and others favoured. The hosts do not react always with the same efficiency or selectivity to all the antigens comprising an infectious agent and accordingly the selection of some of them with detriment to others makes the analysis more specific, but at the expense of a reduced sensitivity, inasmuch as, regardless of the sophistication of the instruments, it is not possible to detect non existent elements in our composition.

In the serological research of some diseases, attempts have been made to solve problems of this type by "neutralizing" or "absorbing" similar but not specific immunological responses against the infectious agent under consideration. These neutralizations or absorptions were carried out with microorganisms similar to but not identical with those investigated. Progress was made in the case of the serological diagnosis of Syphilis by means of Indirect Immunofluorescence and in the case of the Chagas disease for reactivity crossed with Leishmaniasis. However, this method did not spread to other pathologies, whether due to lack of success in the results or due to a marked drop in the serological titers, or of specific responses, after the absorptions.

A different alternative to improve specificity was to work on the mechanisms of the natural or triggered response of the hosts. Several years ago, it was discovered that the immunoglobulins of the IgM type present a more nonspecific behaviour than those termed IgG. Immunoglobulins M are high molecular weight proteins, acting as an immunological ancestor: they are the first to appear in a foetus, the first to appear in an infection and, moreover, they comprise the best part of "natural antibodies". They are found to be active in the polymeric state, and if this is destroyed, the IgM loses nearly all its functions. The IgG molecules are low weight proteins and represent the most perfect and tardiest response of the host. They are active in monomeric state and this allows an easy differentiation from IgM. By means of a gentle reduction method which breaks the disulphide bonds that keep intact the polymeric state of the IgM, this molecule can be deactivated without affecting the IgG. This mechanism has brought about important improvements in the specificity of different serological tests; particularly of agglutination tests of cells or microorganisms. Such is the case of the Direct Agglutination of Chagas and Toxoplasmosis where the present inventor other authors as well, have been able to prove that the systematic use of 2-mercaptoethanol (a gentle reducing agent) allows with acceptable efficiency, presumably normal persons from others who have become infected.

DESCRIPTION OF THE INVENTION

The in-depth exploration of this line of research has led us to the discovery that in the sera of healthy persons there are an important number of nonspecific reagents resistant to the action of 2-mercaptoethanol. That means that such sera continue having an unspecific agglutinating capacity after exposure to the action of 2-mercaptoethanol. Essentially, we have not been able to associate this activity with molecules of the immunoglobulin type and consequently we began to dismiss the antibody function of same. This is a very important discovery for serology, because in the past it was assumed that the reactivity of sera with different types of antigens was based on strictly immunological principles of the antigen-antibody reaction. The direct or indirect proof of other factors creates the possibility of improving the mechanisms of specificity by eliminating this undesirable activity. The presence of nonspecific reagents, even at low titers (i.e., high concentrations of serum or low serological dilutions, for instance: $\frac{1}{2}$; $\frac{1}{4}$; $\frac{1}{8}$) is a source of serious problems regarding serological differentiation, especially when the specific titers are low or when the target is to enhance the sensitivity of the whole system. In these cases the detection of the so-called "background noises" caused by the presence of unspecific reagents is also enhanced. In order to improve the quality of any serological technique it is indispensable to discriminate, as far as possible, between the results corresponding to stimulated population and those corresponding to non stimulated population. In this sense the elimination of nonspecific reagents of any variety represents a substantial advance of serology.

After making sure that the above mentioned unspecific reagents had, among other things, a strong aggregating or agglutinating capacity with regard to animal or vegetal cells or particulate fractions of same, we began to associate this behaviour with that of lectins and proceeded to refer to them as "lectin-like substances".

From the fruits of leguminous plants as well as from other seeds, substances are extracted which are known as lectins and have the capacity of combining spontaneously with carbohydrates comprising more complex molecular structures in microorganisms, animal and vegetal cells present everywhere in nature. As yet the precise function of these substances has not been clarified, although it is probable that among other things they act as glues or cements between cells, but their isolation and use in biology is becoming more and more frequent for the selection of different microorganisms, cells or antigens.

In fact, most cells possess in their inner and outer membranes a high composition in glucids in the form of complex polysaccharides or glycoproteins and glycerophosphatides or phospholipids. When microbial cells, or particulate fractions of same, or animal cells, such as red blood corpuscles, carriers of antigens fixed to their surface, are used as antigenic material, for instance, in an agglutination, the presence of nonspecific agglutinating factors reacting with sugars or phospholipids is plainly shown. The hypothesis of the presence in humans of "lectin-like" substances is not far-fetched. Actually, a short time ago proof was given that a glycoprotein termed "laminin" and apparently acting as a cellular "glue" in the basal membranes of all endothelia has a powerful unspecific effect on red blood corpuscles of rams fixed with aldehydes. It should be stressed that this type of red blood corpuscle is a universally known support for hemagglutination antigens and that laminin is practically sure to be found in circulation, apart from being present in large proportions in the tissues.

The reactivity with membranes through glycerophosphatide components is a known fact of a different non immunological reactive factor such as *Reactive Protein C*. The study of the coupling capacity of Reactive Protein C with substances containing terminal choline has resulted in the conclusion that it can be inhibited by this particular type of molecule—especially phosphatidyl choline. The principal novelty of our discovery consisted in ascertaining that the nonspecific serological reactivities capable of causing false positive or reactive results in among other things agglutination tests of cells or particulate fractions of same, can be eliminated to a great extent by introducing into the reactions simple substances which through inhibition, competition, absorption, neutralization or blocking prevent the aggregating effect of nonspecific reagents of the "lectin-like" type or of the Reactive Protein C type. Sugars are such substances, especially aminated sugars, glycerophosphatides or phospholipids, choline esters, choline salts and sphingomyelins. They act on the mechanisms of non specific coupling with membrane components, during the serological verification process of specific antibodies against antigens forming part of cells or fixed in same.

The nonspecific factors to which we refer are as a rule not only resistant to 2-mercaptoethanol, with the exception of Reactive Protein C, but moreover heat-resistant at the inactivation temperature of agglutinating fractions of the complement such as Clq, i.e. at 56° C. during 30'. It is thus possible to ascertain that the non specific agglutinability elimination effect continues in evidence after exposure of the sera to the described heating.

In practice, the presence of nonspecific factors of the above mentioned type is shown and neutralized by the so-called inhibition methodology. This consists in using reagents formed by two independently acting components which one after the other, or simultaneously, make contact with the serum or humour to be studied.

With this procedure, whether due to the sequence or to the diffusion and combination rate, the first component to make contact with the serum is the sugar or the mixture of sugars and other simple substances which, although having no antigenic activity, should neutralize the "lectin-like" substances and/or nonspecific agglutinants. The neutralized serum reacts with the antigen under consideration, whether forming part of cells, particulate fractions of same or fixed in them. The neutralization of "lectin-like" substances and/or nonspecific agglutinants is ascertained by the quantification of the "inhibition", that is, the quantity of titers obtained with sera of normal persons when the neutralizer is present in the reaction. At the same time, this effect should not be registered or should be minimal in the serum of persons containing specific antibodies against the antigen under consideration, particularly if the serum is deactivated at 56° C. for 30 minutes.

A different kind of serological research was introduced a few years ago for the detection of circulating antigens. In this method, in order to detect an infection, the presence in the host of fractions or components of the microorganism is investigated. When this is confirmed, the probabilities of obtaining a correct specific diagnosis are much better than when an antibody is shown to be present. The detection of antigens is also carried out in sera or humours. The diagnosing instrument in this case, unlike the one described at the beginning, is a specific antibody. In spite of that, the lectin-like substances continue to interfere with the diagnosis because of their ability to react with the specific antibody or with its supports as if it were a case of any other antigenic type molecule. It should not be overlooked that the antibodies also contain sugars and that currently the preferred cellular antibody supports are bacteria such as the staphylococcus, rich in protein A, or the red blood corpuscles fixed with aldehydes.

SPECIFIC DESCRIPTION OF REAGENTS

The following is a description of different reagents prepared according to the invention.

EXAMPLE NO. 1

Elimination of nonspecific reactivities in the detection of antibodies for *Trypanosoma cruzi* in sera of normal persons. An antigen additive for phosphoryl choline and galactose solution is used.

Preparation of the Reagent:

3 g of epimastigots of a 4-day growth of *T. cruzi* culture are collected.

The parasites are repeatedly washed with buffered saline solution, pH 7.8. After a fifth washing the protozoa are resuspended 1/100 in distilled water and left in suspension for one hour.

Having thus produced a cellular lysis, the preparation is at 10,000 r for 20 minutes and the supernatant is isotonized with a five times concentrated buffered saline solution, pH 6.4. This is the antigenic solution which will ultimately be fixed to the formulated corpuscles.

Fixed corpuscles:

A suspension of red blood corpuscles of rams is repeatedly washed with buffered saline solution, pH 7.8, until all traces of hemolysis have disappeared. Resuspended in the same solution at 10% the mass of red blood corpuscles is mixed with an equal volume of saline solution in 10% formol. The mixture is incubated for one hour at 37° C.

The cells fixed by means of this method are washed and again resuspended in buffered saline solution, pH 7.8, with 20% formol.

After a further incubation during one hour at 37° C. the cells are repeatedly washed until all traces of formol have been eliminated. Under such conditions the corpuscles are incubated in a 10% concentration with a suitable concentration of tannic acid of around 1/10000 (which can vary for each lot of corpuscles) and the mixture is left at 37° C. during further 30 minutes. After this treatment the red blood corpuscles are washed three times with a buffer of phosphates, pH 7.8. Lastly, the cells thus resuspended in phosphate buffer, pH 6.4, are mixed with an equal volume of antigen (prepared as described at the beginning). This mixture is kept in incubation during one hour. The antigen which has not become fixed is washed out three times with buffer, pH 7.8. This is the sensitized cellular suspension which will be used in the tests after undergoing a polymerization process with 2% glutaric aldehyde during ½ hour.

To this reagent preparation 2% galactose and 3% phosphoryl choline are added; as an alternative, the same inhibitors can be used in the serum diluting solutions without causing modifications in the results.

The results obtained in sera of healthy persons and persons carrying the infection will now be set forth. The elimination of nonspecific reactivities in the detection of antibodies for *T. cruzi* in sera of normal persons is carried out. A hemagglutination antigen, to which galactose and phosphoryl choline solution has been added, is used.

with the hemogglutination antigens. Actually, such reactivities evidenced as an unspecific agglutinating power should not exist in sera of non Chagasic persons; their presence is an indication of non specific antibodies or "lectin-like" substances. When the test is repeated with serums neutralized with galactose and phosphoryl choline, this nonspecific reactivity largely disappears. When the same kind of study is carried out with persons which are really infected, the agglutinating titers are not modified precisely because they are the product of the action of real antibodies.

EXAMPLE NO. 2

A similar approach is used in the detection of antibodies in Hepatitis B.

Procedure for the preparation of the reagent:

A suspension of red corpuscles according to the methods described in the foregoing example is prepared and subsequently antibodies purified against the surface antigen of Hepatitis B(HBs) are caused to adhere to their surface.

The pure antibodies are obtained by affinity chromatography. To this end an activated sepharose column is prepared, in which protein corresponding to antigen HBs is covalently fixed.

A horse serum hyperimmunized with the same virus is flowed through the column. The column is repeatedly washed with buffer phosphates, pH 7.8, in order to eliminate all traces of proteins that have not been fixed. Subsequently a buffer solution, pH 3, of hydrochloric acid/glycine is flowed through the column. Thus it is possible to break the antigen/antibody bond and pure antibody is collected and quickly stabilized in an alkaline pH.

With a concentration of 2 mg/ml of antibody and red corpuscles, previously treated with 2.5% glutaraldehyde, a mixture is prepared which is left to incubate in the refrigerator (4° C.) for 24 hours. The excess which has not become fixed is repeatedly washed and the remainder is the suspension of cells which will be used as reagent upon adding to it inhibitors of "lectin-like" substances. In this case, the inhibitors are 1% lecithin and 4% glucosamine, and as in the foregoing case they can be found in substitution in the sample diluting solution. The following tests are carried out with these reagents:

TABLE II

| | Serum No. | | TITERS | | | | | | | | |
|---|---|---|---|---|---|---|---|---|---|---|---|
| | | | 2 | 4 | 8 | 16 | 32 | 64 | 128 | 256 | 512 |
| Sera healthy persons | 182 | Inhib. | 138 | 41 | 3 | | | | | | |
| | | No inhib. | 16 | 20 | 45 | 48 | 39 | 14 | | | |
| Sera carriers | 47 | Inhib. | | | | | | | 16 | 18 | 13 |
| | | No inhib. | | | | | | | 16 | 18 | 13 |

As can be seen from the foregoing table, the sera of healthy persons have titers of nonspecific agglutinating

TABLE I

| | Serum No. | | TITERS | | | | | | | | |
|---|---|---|---|---|---|---|---|---|---|---|---|
| | | | 2 | 4 | 8 | 16 | 32 | 64 | 128 | 256 | 512 |
| Sera healthy persons | 269 | No inhib. | 24 | 42 | 50 | 48 | 39 | 26 | 19 | 15 | 12 |
| | | With inhib. | 183 | 82 | 4 | | | | | | |
| Sera carriers | 58 | No inhib. | | | | 3 | 14 | 8 | 23 | 7 | 3 |
| | | With inhib. | | | | 3 | 14 | 10 | 22 | 6 | 3 |

As may be seen in the above table, the negative sera present reactivities with differing intensities in relation activity having a value similar to that of some of the specific reactivities present in carriers. The use of reagents for neutralizing the "lectin-like" substances clarifies the situation by inhibiting the reactivity of healthy persons and by not affecting that of carriers.

EXAMPLE NO. 3

Similarly, the invention is used in the elimination of reactivities in healthy persons and in carriers of Toxoplasma, using the agglutination reaction of antibodies against fractions of the said parasite.

Preparation of Fast Agglutination Antigen for Toxoplasmosis:

Trophozoites of *Toxoplasma gondii* are extracted from the peritoneum of mice three days after inoculation into an ascistic Ehrlich tumor. The parasites are left to settle and washed repeatedly with buffer phosphate, pH 7.8, finally resulting in the obtention of a humid mass which is resuspended in distilled water at the rate of 2 g per every 100 cc. water. This mixture is kept in the refrigerator during 48 hours and subsequently centrifuged at 3000 rev. for 30 minutes. The dregs are discarded and the supernatant is mixed with 2% microspheres of cellulose nitrate having a diameter of approximately 20 microns. The whole mass is incubated during 12 hours at 4° C. and subsequently washed several times with phosphate buffer, pH 7.8. This suspension of sensitized particles is the Fast Agglutination Antigen of Toxoplasma. It is used in tests of agglutination through sedimentation and the results can be read in 10 minutes. In order to be used the antigen is completed by adding 1% N-acetyl galactosamine and 1% α-phosphatidyl choline; alternatively, the same inhibitors can be found in substitution in the sample diluting solution.

The results of serological titers obtained from healthy persons and from carriers of Toxoplasmosis with or without the aid of inhibitors are displayed in Table III.

TABLE III

| Serum | | No. | TITERS | | | | | | | | | | | |
|---|---|---|---|---|---|---|---|---|---|---|---|---|---|---|
| | | | 2 | 4 | 8 | 16 | 32 | 64 | 120 | 256 | 512 | 1024 | 2048 | 4096 |
| Sera healthy persons | 214 | No inh. | 17 | 30 | 32 | 28 | 53 | 26 | 12 | 8 | 2 | | | |
| | | With inh. | 82 | 68 | 53 | 10 | 1 | | | | | | | |
| Sera carriers | 114 | No inh. | | | | | | 8 | 27 | 28 | 37 | 6 | 4 | 4 |
| | | With inh. | | | | | | 8 | 28 | 32 | 32 | 6 | 4 | 4 |

In this case, as can be seen in the table as well as in the foregoing examples, the effect of the simple inhibitor substances is very much in evidence due to the elimination of undesirable unspecific reactivities.

EXAMPLE NO. 4

So far the invention has been described with a view to obtaining serological reagents having a high specificity and sensitivity based on the neutralization, absorption, blocking or inhibition of nonspecific agglutinating factors with simple non antigenic substances. The characterizing feature of such reagents is that some of these simple substances are capable of interacting more readily with the nonspecific agglutinating factors than the antigens or antibodies themselves, due to their affinity or higher speed of diffusion.

Nevertheless, the list of names given in the foregoing examples can be extended to include future discoveries of new nonspecific agglutinating factors and simple elements capable of unblocking them.

However, regardless of all this, some molecular structures, due to the similarity of configuration between them and the above mentioned substances, possess, by simple deduction, the theoretical possibility of substituting the former in identical inhibiting activities. In fact, such is the case of choline salts and of other quaternary ammonium salts, in which the substitution of a radical should not necessarily affect the function of blocking nonspecific agglutinating factors of the Reactive Protein C type, or any other similar agglutinant capable of interaction with choline molecules.

The foregoing was duly tested in runs similar to those described above, using ammonium salts, such as diethyl methyl propyl ammonium bromide, glycidyl trimethyl ammonium chloride, hexadecyl trimethyl ammonium chloride and some of the so-called cationic detergents based on quaternary ammonium salts.

A hemagglutination antigen for Chagas was used, formed by a suspension of red blood corpuscles of rams fixed with aldehydes and sensitized with extracts of epimastigots of *T. cruzi* to which 1% glucosamine and 3% glycidyl trimethyl ammonium chloride was added.

Normal sera were tested with and without inhibitors and the same study was carried out with chronic sera.

TABLE IV

| Sera | | 2 | 4 | 8 | 16 | 32 | 64 | 128 | 256 | 512 | 1024 |
|---|---|---|---|---|---|---|---|---|---|---|---|
| Normal | Without inh. | 24 | 42 | 50 | 48 | 39 | 26 | 19 | 15 | 12 | |
| | With inh. | 80 | 64 | 60 | 42 | 21 | 2 | | | | |
| Chronic | Without inh. | | | 3 | 14 | 8 | 23 | 7 | 3 | | |
| | With inh. | | | 3 | 14 | 10 | 22 | 6 | 3 | | |

As can be seen in the foregoing table, with this simple substance too an inhibiting effect is achieved on nonspecific agglutinating factors present in normal sera, without, however, affecting those caused by specific agglutination in sera of patients suffering from a chronic infection. These tests indicate that the inhibiting effect of choline salts is greater than that of the other quaternary ammonium salts that have been tested. This is probably due to the fact that the latter could not be used at concentrations similar to those of the former because they were more apt to cause self-agglutination phenomena of red blood corpuscles than choline.

What I claim is:

1. A method for improving the specificity of agglutination assays for antigens and antibodies using cellular carriers, the improvement comprising adding to the material to be assayed an inhibitor of non-specific agglutination comprising a sugar.

2. The method of claim 1 wherein the inhibitor comprises a sugar and in addition a compound selected from the group consisting of glycerophosphates, sphingomyelins, choline esters, choline salts, and mixtures thereof.

3. The method of claim 2 wherein the sugar is an aminated sugar.

4. The method of claim 2 wherein the inhibitor is galactose and phosphoryl choline.

5. The method of claim 2 wherein the inhibitor is N-acetyl galactosamine and α-phosphatidyl choline.

* * * * *